United States Patent [19]

Egel-Mitani et al.

[11] Patent Number: 6,110,703
[45] Date of Patent: Aug. 29, 2000

[54] METHOD FOR THE PRODUCTION OF POLYPEPTIDES

[75] Inventors: Michi Egel-Mitani, Vedbæk; Jakob Brandt, Brønshøj; Knud Vad, Frederiksberg, all of Denmark

[73] Assignee: Novo Nordisk A/S, Bagsværd, Denmark

[21] Appl. No.: 08/888,381

[22] Filed: Jul. 7, 1997

Related U.S. Application Data

[60] Provisional application No. 60/021,566, Jul. 11, 1996.

[30] Foreign Application Priority Data

Jul. 5, 1996 [DK] Denmark ................................ 0749/96

[51] Int. Cl.⁷ .......................... C12P 21/00; C12N 15/74; C12N 15/80; C07H 21/04
[52] U.S. Cl. .................... 435/69.1; 435/69.4; 435/255.1; 435/254.2; 435/471; 536/23.1
[58] Field of Search ................................ 435/69.1, 69.4, 435/255.1, 255.2, 471; 536/23.1

[56] References Cited

U.S. PATENT DOCUMENTS 5,179,003  1/1993  Wolf et al. ............................ 435/69.1
5,679,544  10/1997  Fleer et al. ............................ 435/69.1

FOREIGN PATENT DOCUMENTS 0 206 783  12/1986  European Pat. Off. .
WO 85/03949  9/1985  WIPO .
WO 92/17595  10/1992  WIPO .
WO 95/23857  9/1995  WIPO .................................. 435/69.1

OTHER PUBLICATIONS

Azaryan et al. Characterisics of Yap3, a new prohormone processing aspartic protease from S. cerevisiae. Acv. Exp. Med. and Biol. vol. 362:569–572, Dec. 1995.

Komano et al. Shared functions in vivo of a glycosyl–phosphatidylinositol–linked aspartyl protease, Mkc7, and the proprotein processing protease Kex2 in yeast. PNAS Vo. 92:10752–10756, Nov. 1995.

Gabrielsen et al., (1990) Gene 90:255–262.

Egel–Mitani et al., (1990) Yeast 6:127–137.

*Primary Examiner*—Robert A. Schwartzman
*Assistant Examiner*—William Sandals
*Attorney, Agent, or Firm*—Steve T. Zelson, Esq.; Reza Green, Esq.

[57] ABSTRACT

The present invention relates to a novel method for the production of short chain polypeptides, including polypeptides having up to 3 disulfide bonds and/or structures rich in basic amino acid residues, and open structured short chain polypeptides, e.g. glucagon, glucagon like peptides and their functional analogues, in genetically modified yeast cells, said genetically modified yeast cells, and a method for the preparation of said yeast cells.

19 Claims, 6 Drawing Sheets

```
                    SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
           (A) LENGTH: 41 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:1:

Gln Pro Ile Asp Asp Thr Glu Ser Asn Thr Thr Ser Val Asn Leu
1               5                  10                  15

Met Ala Asp Asp Thr Glu Ser Arg Phe Ala Thr Asn Thr Thr Leu
                20                  25                  30

Ala Leu Asp Val Val Asn Leu Ile Ser Met Ala
                35                  40

(2) INFORMATION FOR SEQ ID NO:2:

(i) SEQUENCE CHARACTERISTICS:
           (A) LENGTH: 52 amino acids
           (B) TYPE: amino acid
```

(C) STRANDEDNESS: single
            (D) TOPOLOGY: linear (ii) MOLECULE TYPE: peptide (ix) SEQUENCE DESCRIPTION: SEQ ID NO:2:

Glu Glu Ile Asp Ile Pro Ile Tyr Glu Lys Lys Tyr Gly Gln Val
1               5                   10                  15

Pro Met Cys Asp Ala Gly Glu Gln Cys Ala Val Arg Lys Gly Ala
                20                  25                  30

Arg Ile Gly Lys Leu Cys Asp Cys Pro Arg Gly Thr Ser Cys Asn
                35                  40                  45

Ser Phe Leu Leu Lys Cys Leu
                50

(2) INFORMATION FOR SEQ ID NO:3:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: peptide (ix) SEQUENCE DESCRIPTION: SEQ ID NO:3:

Ser Glu Glu Pro Pro Ile Ser Leu Asp Leu Thr Phe His Leu Leu
1               5                   10                  15

Arg Glu Val Leu Glu Met Ala Arg Ala Glu Gln Leu Ala Gln Gln
                20                  25                  30

Ala His Ser Asn Arg Lys Leu Met Glu Ile Ile
                35                  40

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:4:

Met Ala Lys Arg
1

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:5:

Asp Asp Asp Asp Lys
1               5

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:6:

Met Ala Xaa Lys Arg
1               5

(2) INFORMATION FOR SEQ ID NO:7:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (xi) SEQUENCE DESCRIPTION: SEQ ID NO:7:

GATCGAACGG CCATGAAAAA TTTGTACTAG CTAACGAGCA AAGCTTTTCA ATTCAAT            57

(2) INFORMATION FOR SEQ ID NO:8:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (xi) SEQUENCE DESCRIPTION: SEQ ID NO:8:

CCAGAATTTT TCAATACAAT GGGGAAGTTG TCGTATTTAT AAGCTTTTTC TTTCCAA            57

(2) INFORMATION FOR SEQ ID NO:9:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO:9:

Met Ala Arg Ser Lys Arg
1               5

(2) INFORMATION FOR SEQ ID NO:10:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO:10:

Met Ala Arg Lys Lys Arg
1               5

(2) INFORMATION FOR SEQ ID NO:11:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO:11:

Met Ala Arg Glu Lys Arg
1               5

(2) INFORMATION FOR SEQ ID NO:12:

(i) SEQUENCE CHARACTERISTICS:
            (A) LENGTH: 6 amino acids
            (B) TYPE: amino acid (C) STRANDEDNESS: single
        (D) TOPOLOGY: linear (xi) SEQUENCE DESCRIPTION: SEQ ID NO:12:

Met Ala Glu Arg Leu Glu
1               5

(2) INFORMATION FOR SEQ ID NO:13:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:13:

Met Ala Glu Arg Leu Glu
1               5

(2) INFORMATION FOR SEQ ID NO:14:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO:14:

Trp Ile Ile Ala Glu Asn Thr Thr Leu Ala Asn Val Ala Met Ala Lys
1               5                   10                  15
Arg

METHOD FOR THE PRODUCTION OF POLYPEPTIDES

CROSS-REFERENCE TO RELATED APPLICATIONS

This application claims priority under 35 U.S.C. 119 of Danish application 0749/96 filed Jul. 5, 1996 and U.S. application Ser. No. 60/021,566 filed Jul. 11, 1996, the contents of which are fully incorporated herein by reference.

FIELD OF THIS INVENTION

The present invention relates to a novel method for the production of short chain polypeptides, including polypeptides having up to 3 disulfide bonds and/or structures rich in basic amino acid residues, and open structured short chain polypeptides, e.g. glucagon, glucagon like peptides and their functional analogues, in genetically modified yeast cells, said genetically modified yeast cells, and a method for the preparation of said yeast cells.

BACKGROUND OF THIS INVENTION

Expression of heterologous proteins in yeast after transformation of yeast cells with suitable expression vectors comprising DNA sequences coding for said proteins has been successful for many species of polypeptides, such as glucagon, glucagon like peptides and their functional analogues. Yeasts, and especially Saccharomyces cerevisiae, are preferred host microorganisms for the production of pharmaceutically valuable polypeptides due to the stable yield and safety.

However, it is often found that the expression product is a heterogeneous mixture of species of the desired polypeptide precursor having different amino acid chain lengths. A number of proteases, activated by the PEP4 gene product are responsible for yeast protein degradation. Mutation in the PEP4 gene such as the pep4-3 mutation is often used to reduce cellular proteolysis whereby the quality and yields of heterologous proteins of interest can be improved. EP 341215 describes the use of a yeast strain that lacks carboxypeptidase ysca activity for the expression of the heterologous protein hirudin. Wild-type yeast strains produce a mixture of desulphatohirudin species differing in the C-terminal sequence due to the post-translational action of endogeneous yeast proteases on the primary expression product. It is shown that yeast mutant strains lacking carboxypeptidase ysca activity are unable to remove amino acids from the C-terminus of heterologous proteins and therefore give rise to integral proteins.

The use of yeast strains defective in protease A, B, Y, and/or S activity can only partially reduce random proteolysis of foreign gene products.

Another problem encountered in production of heterologous proteins in yeast is low yield, presumably due to proteolytic processing both in intracellular compartments and at the plasma membrane caused by aberrant processing at internal sites in the protein e.g. secretion of human parathyroid hormone (Gabrielsen et al. Gene 90: 255–262, 1990; Rokkones et al. J. Biotechnol. 33: 293–306, 1994), and secretion of β-endorphine by S. cerevisiae (Bitter et al. Proc. Natl. Acad. Sci. USA 81: 5330–5334, 1984). Some polypeptides, e.g. polypeptides having from about 10 to about 55 amino acids or shorter chains and none or a few disulphide bonds and/or are rich in basic amino acids, such as β-endorphine, glucagon and glucagon like peptides may be especially susceptible to intracellular and extracellular proteolytic degradation when expressed in a heterologous host due to their short-chain open and non-stable structure resulting in an inhomogeneous product.

WO 95/23857 discloses production of recombinant human albumin (rHA), which is a very large carrier-type protein cross-linked with 17 disulphide bonds and having a molecular weight of about 66 kD, in yeast cells having a reduced level of yeast aspartyl protease 3 (Yap3p) proteolytic activity resulting in a reduction of undesired 45 kD rHA fragment and in a 30 to 50% increased yield of recovered rHA produced by the haploid Δyap3 yeast strain compared to the rHA produced by the corresponding haploid YAP3 wild-type yeast strain.

Previously, Bourbonnais et al. (Biochimie 76: 226–233, 1994), have shown that the YAP3 protease gene product has in vitro substrate specificity which is distinct though overlapping with the Kex2p substrate specificity, and shown that Yap3p cleaves exclusively C-terminal to arginine residues present in the prosomatostatin's putative processing sites. Moreover, Cawley et al. (J. Biol. Chem. 271: 4168–4176, 1996) have determined the in vitro specificity and relative efficiency of cleavage of mono- and paired-basic residue processing sites by Yap3p for a number of prohormone substrates, such as bovine proinsulin.

The purpose of the present invention is to provide an improved method for the production of secreted polypeptides having up to about 55 amino acids, preferably from 10–50 amino acids, more preferably from 15–40 or preferably from 25–35 amino acids in the polypeptide chain, and having from 0 to 3 disulphide bonds, preferably no more than one disulphide bond, in the structure in-a yeast expression system. Preferred examples of polypeptides are glucagon and glucagon like peptides, CRF, and truncated and/or C-or N-terminally truncated and/or N-terminally extended forms of cocaine amphetamine regulated transcript (CART). Preferably, the production of polypeptides according to the invention is considerably increased, e. g. more than two fold compared to the production of said polypeptides in conventional yeast expression systems.

Often it is advantageous to produce heterologous polypeptides in a diploid yeast culture, because possible genetical defects may become phenotypically expressed in a haploid yeast culture, e.g. during continuous fermentation in production scale, and because the yield may be higher (Fu et al. Biotechnol. Prog., 12: 145–148, 1996; Mead et al. Biotechnol. Letters, 8: 391–396, 1986).

It would be obvious for a person skilled in the art to use the method of the present invention to produce other polypeptides satisfying the above criteria, such as insulin and insulin analogues, adrenocorticotropic hormones, angiotensinogen, atrial natriuretic peptides, dynorphin, endorphines, galanin, gastrin, gastrin releasing peptides, neuropeptide Y fragments, pancreastatin, pancreatic polypeptides, secretin, vasoactiv intestinal peptide, growth hormone releasing factor, melanocyte stimulating hormone, neurotensin, adrenal peptide, parathyroid hormone and related peptides, somatostatin and related peptides, brain natriuretic peptide, calcitonin, corticotropin releasing factor (CRF) (SEQ ID NO: 3), thymosin, and urotensin; and homologous or otherwise related peptides and fragments of these and other polypeptides (e.g. EEID-CART$_{55-102}$ (SEQ ID NO: 2)), as long as the criteria of having up to 55 amino acids, preferably from 10–50 amino acids, more preferably from 15–40 or from 25–35 amino acids in the polypeptide chain, and having from 0 to 3 disulphide bonds, preferably no more than one disulphide bond in the structure, is fulfilled.

SUMMARY OF THE INVENTION

The above identified purpose is achieved with the method according to the present invention which comprises culturing a yeast which has reduced activity of Yap3 protease (Yap3p) or a homologue thereof and has been transformed with a hybrid vector comprising a yeast promoter operably linked to a DNA sequence coding for a polypeptide having up to 55 amino acids, preferably from 10–50 amino acids, preferably from 15–40, or from 25–35 amino acids in the polypeptide chain, and having from 0 to 3 disulphide bonds, preferably no more than one disulphide bond in the structure, such as glucagon or glucagon like peptides, and isolating said polypeptides. Preferably, the yeast cells lack Yap3p activity through disruption of the YAP3 gene.

Using a YAP3 disrupted yeast strain for the production of polypeptides having from 1–70 amino acids, preferably from 1–40, and more preferably from 10–30 amino acids in the polypeptide chain, and having no more than one disulphide bonds in the structure such as polypeptides encoded by the glucagon precursor gene including glucagon, GRPP, GLP-1, GLP-2, and their functional analogues thereof result in a remarkably improved yield of up to about 2-fold and even 10-fold compared to the yield from the corresponding YAP3 wild-type yeast strain. It has been found that using a YAP3 disrupted yeast strain for the production of heterologous polypeptides having up to 55 amino acids, preferably from 10–50 amino acids, preferably from 15–40 or from 25–35 amino acids, in the polypeptide chain, and having from 0 to 3 disulphide bonds, preferably no more than one disulphide bond in the structure, such as polypeptides encoded by the glucagon precursor gene including glucagon, GRPP, GLP-1, GLP-2, and their functional analogues thereof or CRF, e.g. as shown in SEQ ID NO:3 herein, or truncated and/or N-terminally extended forms of CART, preferably EEID-CART$_{55-102}$ (SEQ ID NO:2), result in a remarkably improved yield of the heterologous polypeptide of up to about 2-fold and even 10-fold compared to the yield obtained from the corresponding YAP3 wild-type yeast strain. Another advantage of using the method of the invention for production of heterologous polypeptides is that the secreted product has an improved homogenicity due to a reduced degree of proteolytic degradation.

The present inventors have also found that the use of a diploid YAP3 disrupted yeast in the method of the invention results in a significantly higher production level of secreted heterologous polypeptide which is about 2-fold and even 9-fold higher compared to the yield level from the corresponding wild-type haploid yeast.

Suitably, the yeast is *S. cerevisiae* which lacks a functional YAP3 gene. However, other yeast genera may have equivalent proteases, i.e. homologues of Yap3p, e. g. the genera Pichia and Kluyveromyces as shown in WO 95/23857 and Clerc et al. (J. Chromat. B. 662: 245–259, 1994). A gene is regarded as a homologue, in general, if the sequence of the translation product has greater than 50% sequence identity to Yap3p. Komano and Fuller (Proc. Natl. Acad. Sci, USA 92: 10752–10756, 1995) has identified the Mkc7 aspartyl protease from *S. cerevisiae* which is closely related to Yap3p (53% identity). Other aspartyl proteases of Saccharomyces include the gene products of PEP4, BAR1, and of open reading frames, the sequences of which are partially homologous with the YAP3 open reading frame, such as YAP3-link (coded by GenBank acc. No. X89514: pos. 25352–26878), YIV9 (Swiss Prot acc. No. P40583), and aspartyl protease (IV) (coded by GenBank acc. No. U28372: pos. 326–2116). According to recently accepted yeast genome nomenclature the yeast gene names YAP3, YAP3 link, YIV 9, NO 4, and MKC 7 used herein correspond to the yeast open reading frame YLR120C, YLR121C, YIRO39C, YDR349C, and YDR144C, respectively. Furthermore, the gene product of open reading frame YGL259W is included among the yeast aspartyl proteases.

Examples of yeasts include *Saccharomyces cerevisiae, Saccharomyces kluyveri, Schizosaccharomyces pombe, Kluyveromyces lactis, Hansenula polymorpha, Pichia pastoris, Pichia methanolica, Pichia kluyveri, Yarrowia lipolytica,* Candida sp., *Candida utilis, Candida cacaoi,* Geotrichum sp., and *Geotrichum fermentans.*

A suitable means of eliminating the activity of a protease is to disrupt the host gene encoding the protease, thereby generating a non-reverting strain missing all or part of the gene for the protease including regulatory and/or coding regions, or, alternatively, the activity can be reduced or eliminated by classical mutagenesis procedures or by the introduction of specific point mutations. Other methods which may be suitable for down regulation of the protease include the introduction of antisense and/or ribozyme constructs in the yeast, e.g. Atkins et al. (Antisense and Development 5: 295–305, 1995) and Nasr et al. (Mol. Gen Genet 249: 51–57, 1995). One preferred method of disrupting the YAP3 gene in the yeast strain used in the method of the present invention are described by Rothstein (Method in Enzymol, 194: 281–301, 1991).

The expression "glucagon or glucagon like peptides" as used herein may be of human origin or from other animals and recombinant or semisynthetic sources and include all members of the glucagon family, such as GRPP (glicentine related polypeptide), glucagon, GLP-1 (glucagon like peptide 1), and GLP-2 (glucagon like peptide 2), including truncated and/or N-terminally extended forms, such as GLP-1(7-36), and includes analogues, such as GLP-1(7-35)R36A GLP-2 F22Y, GLP-2 A19T+34Y. GLP-2 A2G and GLP-2 A19T, and other analogues having from 1 to 3 amino acid changes, additions and/or deletions. The cDNA used for expression of the polypeptide according to the invention include codon optimised forms for expression in yeast.

Throughout the description and claims is used one and three letter codes for amino acids in accordance with the rules approved (1974) by the IUPAC-IUB Commission on Biochemical Nomenclature, vide Collected Tentative Rules & Recommendations of the Commission on Biochemical Nomenclature IUPAC-IUB, 2$^{nd}$ ed., Maryland, 1975.

A further aspect of the invention is a culture of yeast cells transformed with a hybrid vector containing a polynucleotide sequence, preferably a DNA sequence, encoding a polypeptide having up to 55 amino acids, preferably from 10 to 50 amino acids, more preferably from 15 to 40, or preferably from 20 to 30 amino acids, most preferably from 25 to 35 amino acids in the polypeptide chain, and having from 0 to 3 disulphide bonds, preferably no more than one disulphide bond in the structure, said polynucleotide sequence or DNA sequence being operably linked to a polynucleotide sequence or DNA sequence encoding a yeast promoter and a leader sequence (pro sequence or prepro sequence) and/or other polynuceotide sequences or DNA sequences that are necessary for said polypeptide to be expressed in and secreted from the yeast, said culture of yeast cells being characterized in that the cells have reduced Yap3p activity, preferably through a disruption of the YAP3 gene, and said culture of yeast cells being a culture of haploid or polyploid, preferably diploid, yeast cells.

In another aspect the invention provides a culture of yeast cells containing a polynucleotide sequence encoding a polypeptide having up to 55 amino acids, preferably from 10–50 amino acids, preferably from 15–40 or preferably from 20–30 amino acids, most preferably from 25 to 35 amino acids, and having from 0 to 3 disulphide bonds, preferably one or less disulphide bonds in the structure, and a second polynucleotide sequence encoding a secretion signal causing said polypeptide to be expressed in and secreted from the yeast, characterized in that the yeast cells have reduced Yap3 protease activity. Preferably, the yeast cells are diploid yeast cells transformed with a hybrid vector comprising said polynucleotide sequences, and preferably the yeast cells lack Yap3p activity which may conveniently be obtained through disruption of the YAP3 gene.

The DNA encoding the polypeptides having up to 55 amino acids, preferably from 10–50 amino acids, preferably from 15–40, or preferably from 25–35 amino acids in the polypeptide chain, and having from 0 to 3 disulphide bonds, preferably no more than one disulphide bonds in the structure, may be joined to a wide variety of other DNA sequences for introduction into an appropriate host. The companion DNA will depend upon the nature of the host, the manner of the introduction of the DNA into the host, and whether episomal maintenance or integration on host chromosome(s) is desired.

Generally, the DNA is inserted into an expression vector, such as a plasmid, in proper orientation and correct reading frame for expression. The vector is then introduced into the host through standard techniques and, generally, it will be necessary to select for transformed host cells.

If integration is desired, the DNA is inserted into an yeast integration plasmid vector, such as pJJ215, pJJ250, pJJ236, pJJ248, pJJ242 (Jones & Prakash, Yeast 6: 363,1990) or pDP6 (Fleig et al. Gene 46:237, 1986), in proper orientation and correct reading frame for expression, which is flanked with homologous sequences of any non-essential yeast genes, transposon sequence or ribosomal genes. Preferably the flanking sequences are yeast protease genes or genes used as a selective marker. The DNA is then integrated on host chromosome(s) by homologous recombination occured in the flanking sequences, by using standard techniques shown in Rothstein (Method in Enzymol. 194: 281–301, 1991) and Cregg et al. (Bio/Technol. 11:905–910, 1993).

Host cells that have been transformed by the recombinant DNA of the invention are then cultured for a sufficient time and under appropriate conditions known to those skilled 20 in the art in view of the teachings disclosed herein to permit the expression and secretion of the polypeptides to be produced according to the method of the invention, preferred examples of polypeptides being glucagon, glucagon like peptides, CRF and EEID-CART$_{55-102}$ (SEQ ID NO:2), or their functional analogues, which can then be recovered, as is known.

Useful yeast plasmid vectors include the POT (Kjeldsen et al. Gene 170: 107–112, 1996) and YEpl3, YEp24 (Rose and Broach, Methods in Enzymol. 185: 234–279, 1990), and pG plasmids (Schena et al. Methods in Enzymol. 194: 289–398, 1991).

Methods for the transformation of S. cerevisiae include the spheroplast transformation, lithium acetate transformation, and electroporation, cf. Methods in Enzymol. Vol. 194 (1991). Preferably the transformation is as described in the examples herein.

Suitable promoters for S. cerevisiae include the MFα1 promoter, galactose inducible promoters such as GAL1, GAL7 and GAL10 promoters, glycolytic enzyme promoters including TPI and PGK promoters, TRP1 promoter, CYCl promoter, CUP1 promoter, PHO5 promoter, ADH1 promoter, and HSP promoter. A suitable promoter in the genus Pichia is the AOXI (methanol utilisation) promoter.

The transcription terminal signal is preferably the 3' flanking sequence of a eucaryotic gene which contains proper signal for transcription termination and polyadenylation. Suitable 3' flanking sequences may, e.g. be those of the gene naturally linked to the expression control sequence used, i.e. corresponding to the promoter.

The DNA constructs that are used for providing secretory expression of the polypeptide according to the invention comprise a DNA sequence that includes a leader sequence linked to the polypeptide by a yeast processing signal. The leader sequence contains a signal peptide ("pre-sequence") for protein translocation across the endoplasmic reticulum and optionally contains an additional sequence ("pro-sequence"), which may or may not be cleaved within yeast cells before the polypeptide is released into the surrounding medium. Useful leaders are the signal peptide of mouse α-amylase, S. cerevisiae MFα1, YAP3, BAR1, HSP150 and S. kluyveri MFα signal peptides and prepro-sequences of S. cerevisiae MFα1, YAP3, PRC, HSP150, and S. kluyveri MFα and synthetic leader sequences described in WO 92/11378, WO 90/10075 and WO 95/34666. Furthermore, the polypeptides to be produced according to the method of the invention may be provided with an N-terminal extension as described in WO 95/35384.

The invention also relates to a method of preparing a yeast having reduced Yap3p activity comprising the steps of a) providing a hybrid plasmid containing a part of the YAP3 gene and suitable for transformation into a yeast cell, b) disrupting the YAP3 gene by deleting the fragment of YAP3 and inserting the URA3 gene instead to obtain a Δyap3::URA3 gene disruption plasmid, c) providing a yeast Δura3 deletion mutant, d) transforming said mutant with said plasmid, and e) selecting the Δyap3::URA3 deletion mutants on a medium without uracil. Further the invention relates to a method of preparing a yeast having reduced Yap3p activity using antisense technology.

Moreover, the polypeptides to be produced according to the method of the invention may conveniently be expressed coupled to an N- or C-terminal tag or as a precursor or fusion protein although the total length of the expressed polypeptide may exceed a total of 55 or 70 amino acids.

DETAILED DESCRIPTION OF THIS INVENTION

Preferred embodiments of this invention are described in Table 1 below. Having knowledge of the art, it will be obvious to a skilled person to produce other polypeptides having up to 55 amino acids, preferably from 10–50 amino acids, preferably from 15–40, or preferably from 25–35 amino acids in the polypeptide chain, and having from 0 to 3 disulphide bonds, preferably no more than one disulphide bond in the structure and their functional analogues by the method of the present invention using similar constructs.

TABLE 1

| Presequence (signal) | Prosequence | Heterologous protein |
|---|---|---|
| MF α1(1–19) | MF α1(20–85) | Glucagon |
| MF α1(1–19) | MF α1(20–81)MAKR (SEQ ID NO:4) | DDDDK (SEQ ID NO:5)-Glucagon |
| MF α1(1–19) | MF α1(20–85) | GLP-1(7–37) |
| YAP3 (1–21) | LA19[1] KR | GLP-1(7–35)R36A |
| spx3[2] | LaC212 | GRPP |
| MF α1(1–19) | MF α1(20–81)MAKR (SEQ ID NO:4) | GLP-2 |
| HSP150 (1–18) | HSP150 (19–67)-WIIAENTTLANVAMAKR (SEQ ID NO:14) | GLP-2 |
| MF α1(1–19) | MF α1(20–81)MAKR (SEQ ID NO:4) | GLP-2 analogue F22Y |
| MF α1(1–19) | MF α1(20–81)MAKR (SEQ ID NO:4) | GLP-2 analogue A19T, +34Y |
| MF α1(1–19) | MF α1(20–81)MAKR (SEQ ID NO:4) | GLP-2 analogue A19T |
| MF α1(1–19) | MF α1(20–81)MAKR (SEQ ID NO:4) | GLP-2 analogue A2G |
| MF α1(1–19) | MF α1(20–81) MAXKR (SEQ ID NO:6) where X is a peptide bond or Y or S or K or E or ARS | Glucagon or Calcitonin |

[1]LA19, cf. SEQ ID NO: 1 herein and WO 95/34666, [2]spx3-LaC212, cf. WO 89/02463 and WO 90/10075.

The Genetic background of *S. cerevisiae* strains used herein is as follows:

E11-3C MATα YAP3 pep4-3 Δtpi::LEU2 leu2 URA3

SY107 MATα YAP3 pep4-3 Δtpi::LEU2 leu2 Δura3

ME1487 MATα Δyap3::URA3 pep4-3 Δtpi::LEU2 leu2 Δura3

ME1656 MATα Δyap3::ura3 pep4-3 Δtpi: :LEU2 leu2 Δura3

ME1684 MATaα Δyap3::URA3::Δylrl121c pep4-3 Δtpi:LEU2 leu2 Δura3

ME1695 MATα Δyap3::ura3 pep4-3 Δtpi::LEU2 leu2 Δura3

ME1719 MATa/α Δyap3::URA3/Δyap3::ura3 pep4-3/pep4-3 Δtpi::LEU2/Δtpi::LEU2 leu2/leu2 Δura3/Δura3

MT663 MATa/α YAP3/YAP3 pep4-3/pep4-3 Δtpi::LEU2/Δtpi::LEU2 leu2/leu2 URA3/URA3 HIS4/his4

The present invention is further illustrated by the following examples which, however, are not to be construed as limiting the scope of protection. The features disclosed in the fore-going description and in the following examples may, both separately and in any combination thereof, be material for realizing the invention in diverse forms thereof.

EXAMPLE 1
Δyap3::URA3 Gene Disruption

Figure 1:
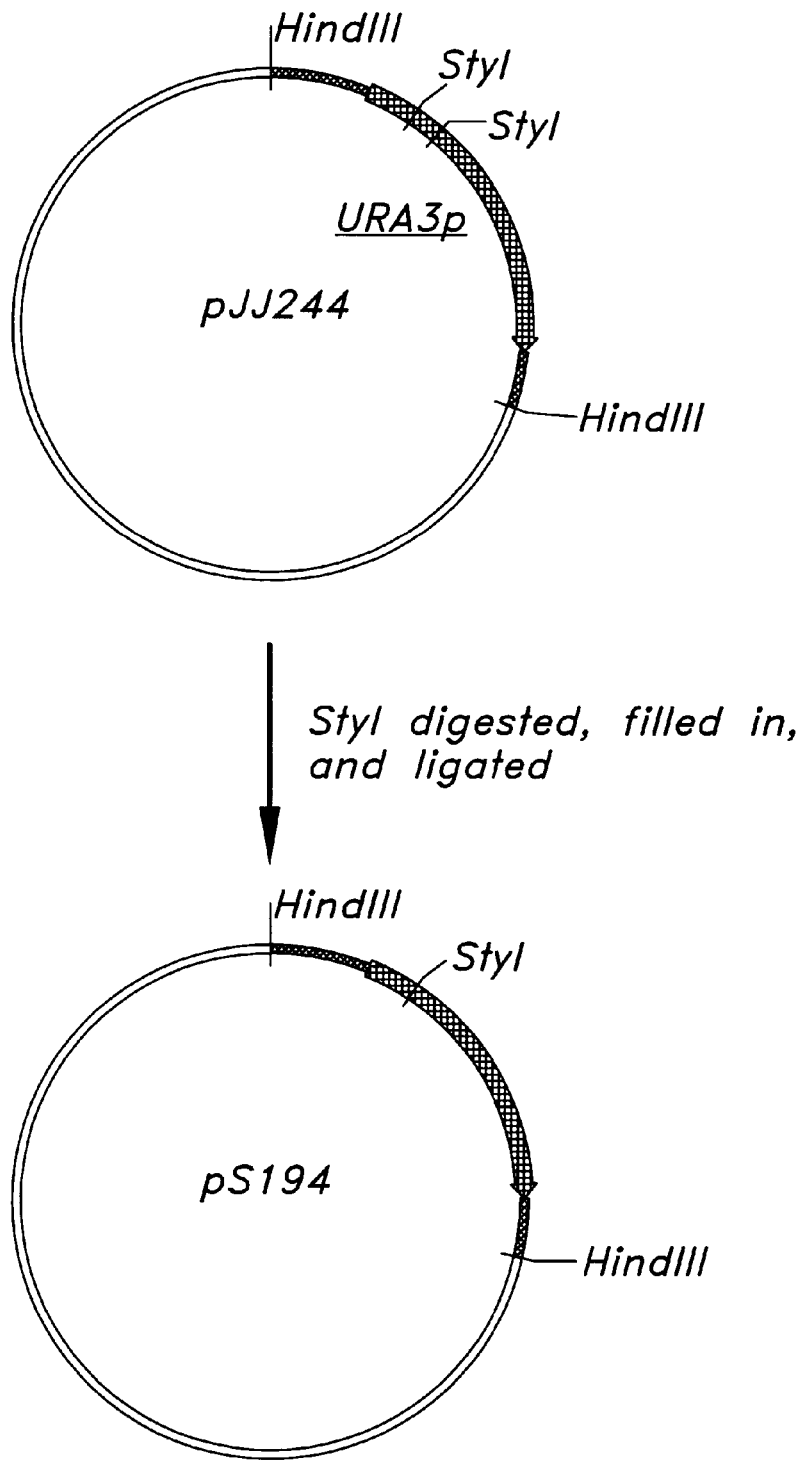
FIG. 1 shows the construction of the pS194 plasmid.

The Δura3 deletion mutation was constructed as follows: pJJ244 (pUC18 containing a 1.2 kb HindIII fragment of the URA3 gene) was digested with StyI and filled in with Klenow polymerase and self ligated. The resulting plasmid designated pS194 contains a 84bp of StyI-StyI fragment deletion of the URA3 gene, cf. FIG. 1.

Figure 2:
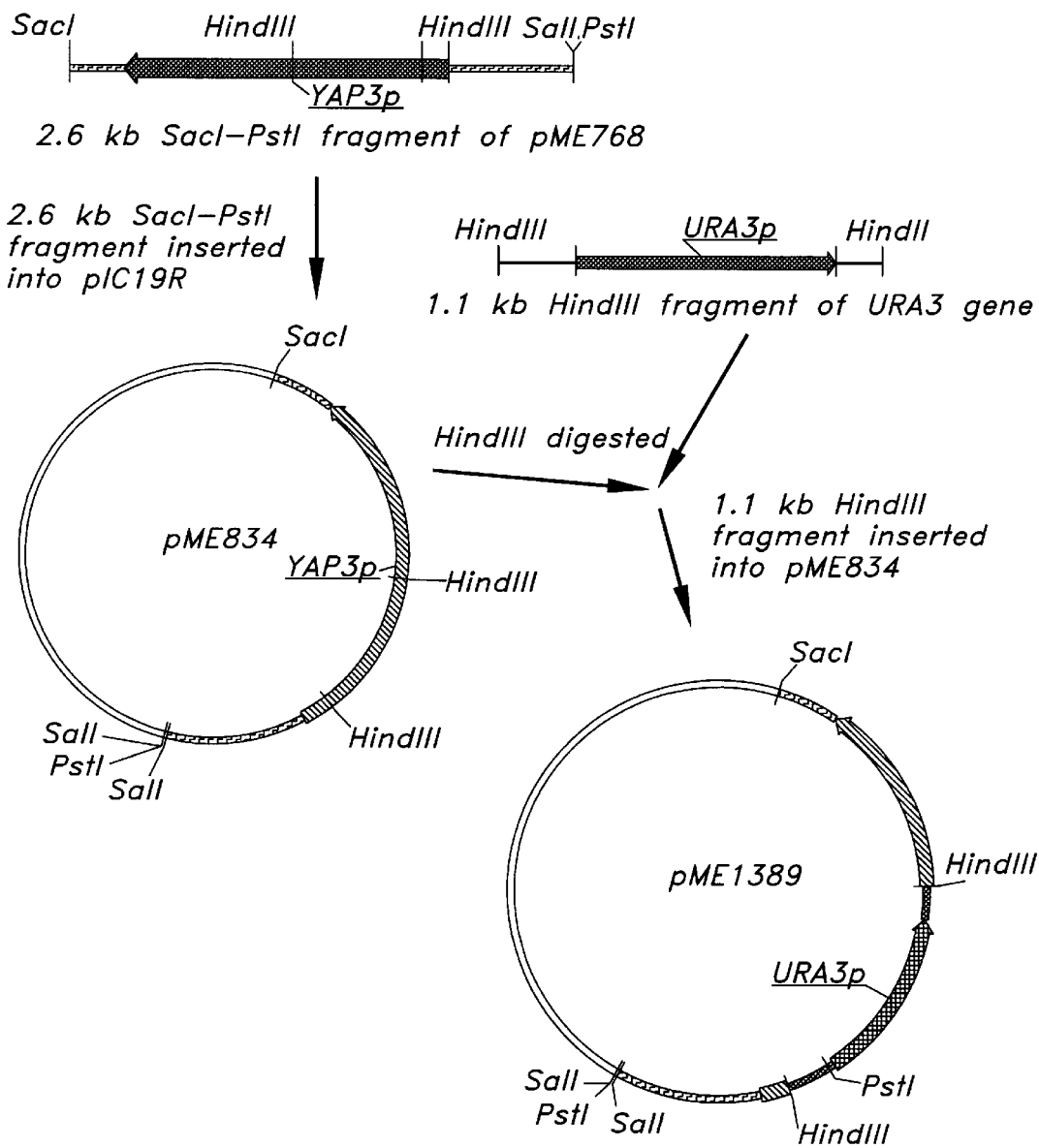
FIG. 2 shows the construction of plasmids pME834 and pME1389.

The Δyap3::URA3 gene disruption plasmid pME1389 was constructed as follows: The 2.6kb SacI-PstI fragment which contains the YAP3 gene in pME768 (Egel-Mitani et al. Yeast 6: 127–137, 1990) was inserted in 2.6 kb of the SacI-PstI fragment of pIC19R (Marsh et al. Gene 32: 481–485, 1984). The resulting plasmid is pME834. pME834 was digested with HindII to form a deletion of the 0.7 kb YAP3 fragment and the 1.2 kb HindIII fragment of the URA3 gene (Rose et al. Gene 29: 113–124, 1984) was inserted instead. The resulting plasmid is pME1389. The construction of plasmids pME834 and pME1389 is shown in FIG. 2 in diagrammatic form.

*S. cerevisiae* strain E11-3C (MATα YAP3 pep4-3 Δtpi::LEU2 leu2 URA3), cf. ATCC 20727, U.S. Pat. No. 4766073, was transformed with linialized pS194 (BsgI digested) to make Δura deletion mutation. By selection on 5-FOA (5-fluoro-orotic acid) containing minimal plates, the Δura3 mutant designated SY107 was obtained.

The strain SY107 (MATα YAP3 pep4-3 Δtpi::LEU2 leu2 Δura3), was then transformed with pME1389 previously being cut by SalI and SacI, and 3kb fragment of Δyap3::URA3 was isolated for the transformation. Δyap3::URA3 deletion mutants were selected on minimal plates without uracil. URA3 transformants were characterized by PCR and Southern hybridisation to confirm the correct integration of the Δyap3::URA3 fragment in the YAP3 locus. ME1487 was isolated as a Δyap3::URA3 deletion mutant (MATα Δyap3::URA3 pep4-3 Δtpi: :LEU2 leu2 Δura3).

EXAMPLE 2
Construction of a Diploid Δyap3/Δyap3 Strain

Figure 6:
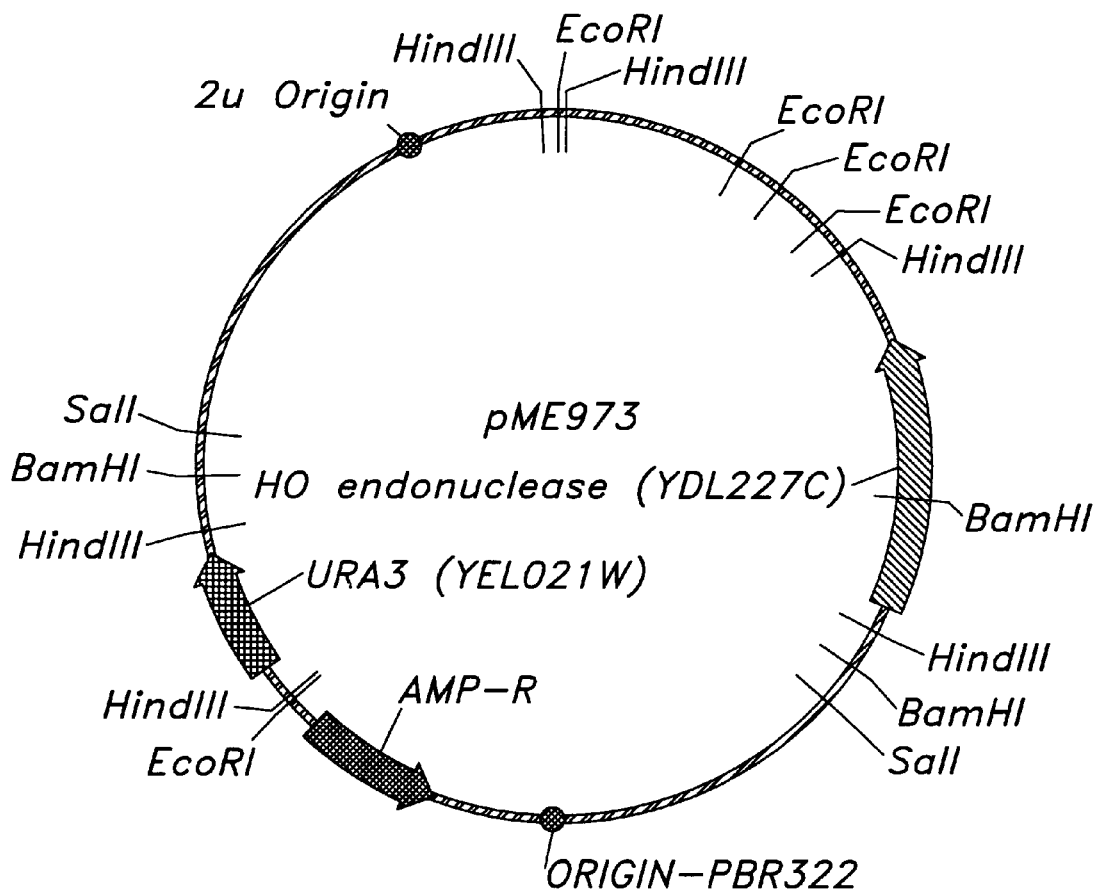
FIG. 6 is a restriction map of the pME973 plasmid, containing the genes encoding the HO (homothallism) endonuclease and Ura3p inserted into the YEpl3 plasmid.

ME1487 was mutagenized by using EMS (methanesulfonic acid ethylester) and ura3 mutants were selected on plates containing 5-FOA. One of the selected isolates, ME1656 was then subjected to mating type switch (Herskowitz and Jensen, Methods in Enzymol. 194: 132–146,1991) by transient transformation with pME973 shown in FIG. 6. pME973 contains the genes encoding the HO (homothallism) endonuclease and URA3 inserted into the YEpl3 plasmid (Rose and Broach, Methods in Enzymol. 185: 234–279, 1990). From transient transformants, ME1695 was selected as the haploid strain, which had switched from MATα to MATa, and have the following genetic background: MATa Δyap3::ura3 pep4-3 Δtpi::LEU2 leu2 Δura3.

ME1695 was then crossed with ME1487 by micromanipulation (Sherman and Hicks, Methods in Enzymol. 194: 21–37, 1991) in order to get Δyap3/Δyap3 diploids. From the resulting diploids, ME1719 was selected as the strain with the following genetic background: MATa/α Δyap3::ura3/Δyap3::URA3 pep4-3/pep4-3 Δtpi::LEU2/Δtpi::LEU2 leu2/leu2 Δura3/Δura.

EXAMPLE 3
Construction of a Δyap3::URA3::Δylrl121lc Double Disruption Strain In order to make a one-step gene disruption strain of the two closely linked genes encoding YAP3 and YLR121C, the following two oligonucleotide primers were synthesized:

P1 Length 57bp: YLR121C/URA3 primer

5'-GAT CGA ACG GCC ATG AAA AAT TTG TAC TAG CTA ACG AGC AAA GCT

TTT CAA TTC AAT-3' (SEQ ID NO:7)

P2 Length 57bp: YAP3/URA3 primer

5'-CCA GAA TTT TTC AAT ACA ATG GGG AAG TTG TCG TAT TTA TAA GCT TTT

TCT TTC CAA-3' (SEQ ID NO:8)

P1 and P2 each contains 40 nucleotides corresponding to sequences within the coding region of YLR121C and YAP3, respectively, as well as a HindIII site (AAGCTT) and 12 nucleotides corresponding to sequences flanking the URA3 gene (YEL021W). P1 and P2 were used for PCR using the URA3 gene as template. The resulting 1248bp PCR fragment contains the URA3 selective marker flanked with 40 nucleotides derived from the YAP3 or YLR121C encoding regions. The PCR fragment was then transformed into ME1655, and Δyap3::URA3::Δylrl121c deletion mutants were selected and characterized as described in Example 1. ME1684 was isolated as a Δyap3::URA3::Δylrl121c mutant with the following genetic background:

MATα Δyap3::URA3::Δylrl121c pep4-3 Δtpi::LEU2 leu2 Δura3.

EXAMPLE 4
Transformation into Yeast

In order to make yeast competent cells, yeast haploid strains SY107 and ME1487 or the diploid ME1719 strain were cultivated in 100 ml YPGGE medium (1% yeast extract, 2% peptone, 2% glycerol, 2% galactose, 1% ethanol) to $OD_{600}=0.2$. Cells were harvested by centrifugation at 2000 rpm for 5 min. and washed once by 10 ml $H_2O$. Cells were resuspended in 10 ml SED (1 M sorbitol, 25 mM $Na_2EDTA$ pH 8, 6.7 mg/ml dithiothreitol) and incubated at 30° C. for 15 min. Cells were harvested by centrifugation and resuspended in 10 ml SCE (1 M sorbitol, 0.1 M Na-citrate, 10 mM $Na_2EDTA$, pH 5.8)+2 mg Novozyme SP234 and incubated at 30° C. for 30 min. After cells were harvested by centrifugation and washed once by 10 ml 1.2 M sorbitol and subsequently by 10 ml CAS (1 M sorbitol 10 mM $CaCl_2$, 10 mM Tris-HCl pH 7.5), cells were harvested by centrifugation and resuspended finally in 2ml CAS. Competent cells were frozen in portion of 100 μl per microfuge tube at −80° C.

Transformation was made as follows: Frozen competent cells (100 μl) were warmed up quickly and 1 μg plasmid DNA were added. Cells were incubated at room temp. for 15 min. and 1 ml PEG solution (20% polyethyleneglycol 4000, 10 mM $CaCl_2$, 10 mM Tris-HCl pH 7.5) was added. After 30 min. at room temperature, cells were harvested by centrifugation at 2000 rpm for 15 min. and resuspended in 100 μl SOS (1 M sorbitol, ½ vol. YPGGE, 0.01% uracil, 7 mM $CaCl_2$). After incubating at 30° C. for 2 hours, cells were centrifuged and resuspended in 0.5 ml 1 M sorbitol. Cells were then spread on YPD plates (1% yeast extract, 2% peptone, 2% glucose, 2% agar) together with 6ml of top agar (YPD containing 2.5% agar). Plates were incubated at 30° C. for 3 to 5 days until transformants appear.

EXAMPLE 5
Heterologous Protein Expression Plasmid

Yeast-*E. coli* shuttle vector used in the following examples contains a heterologous protein expression cassette, which includes a DNA sequence encoding a leader sequence followed by the heterologous polypeptide in question operably placed in between the TPI promoter and TPI terminator of *S. cerevisiae* in a POT plasmid (Kjeldsen et al. 1996, op. cit.). The leader sequences are the MFα1 prepro-sequence and modification thereof. Examples are shown as follows:

TABLE 2

Figure 3:
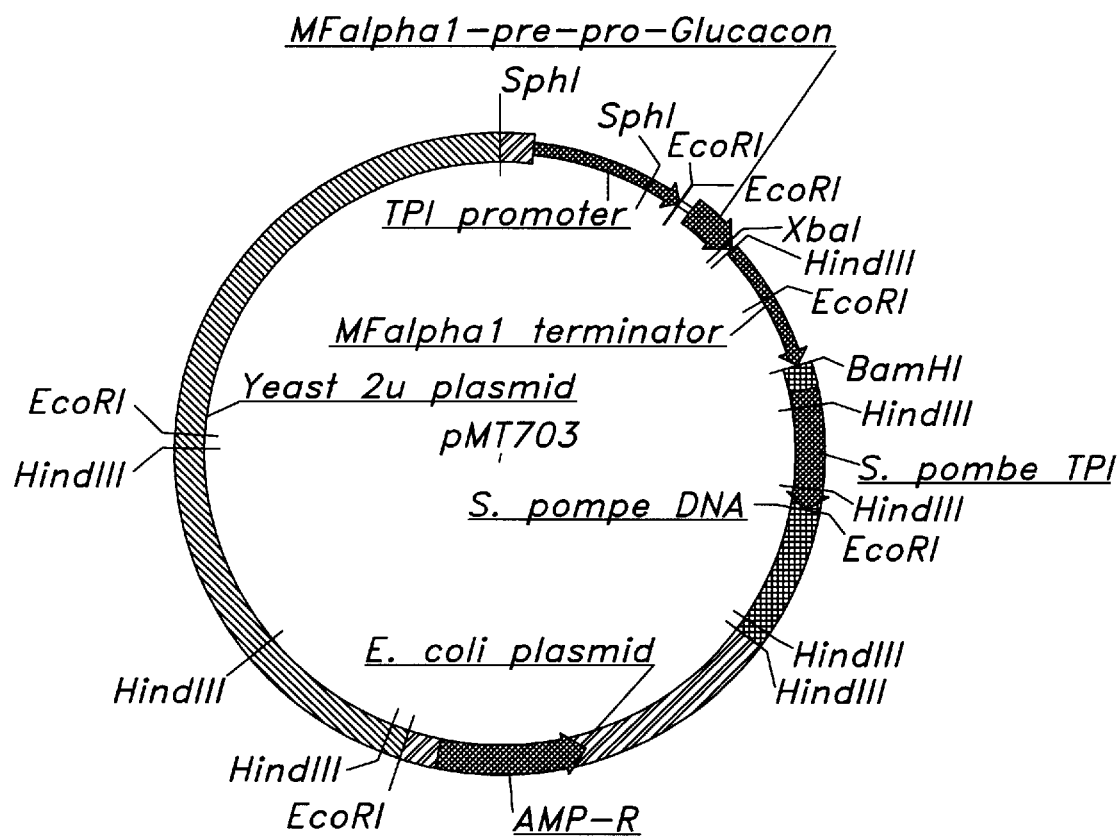
FIG. 3 is a restriction map of the human glucagon expression plasmid pMT703.
Figure 4:
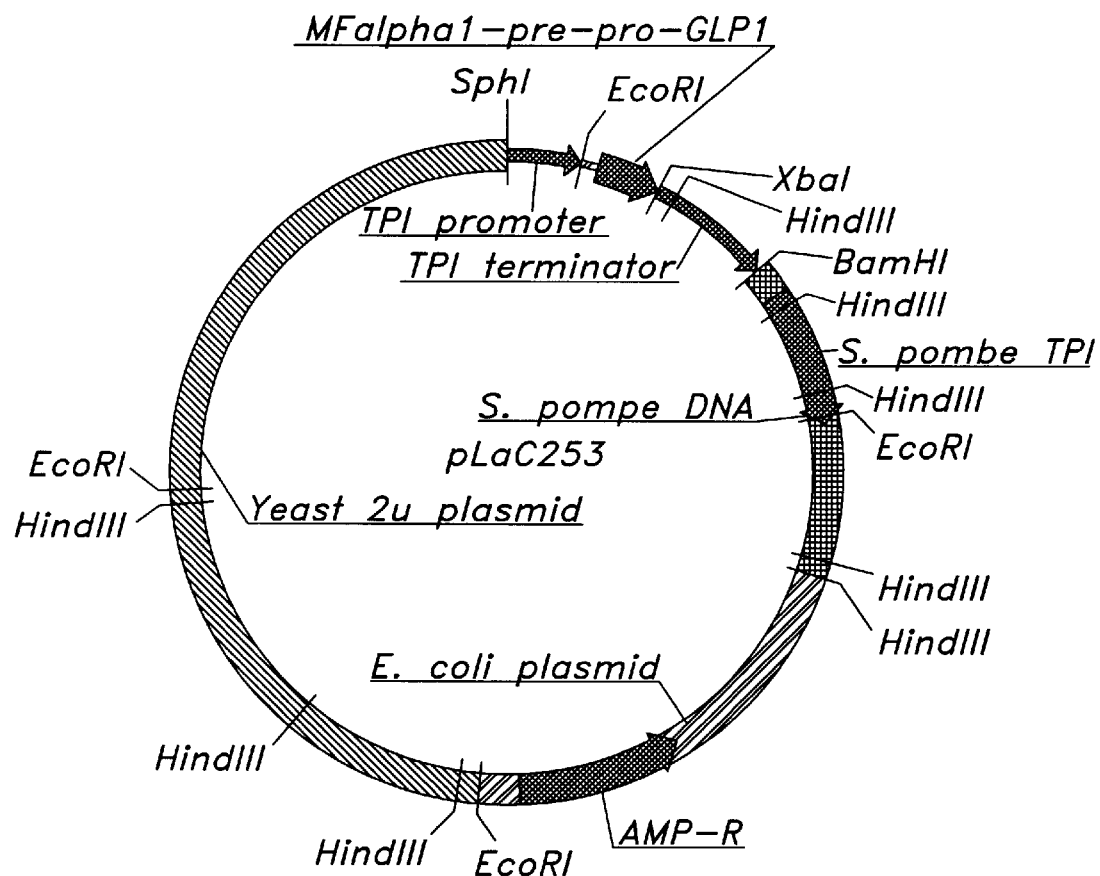
FIG. 4 is a restriction map of the human GLP-1(7-37) expression plasmid pLaC253.
Figure 5:
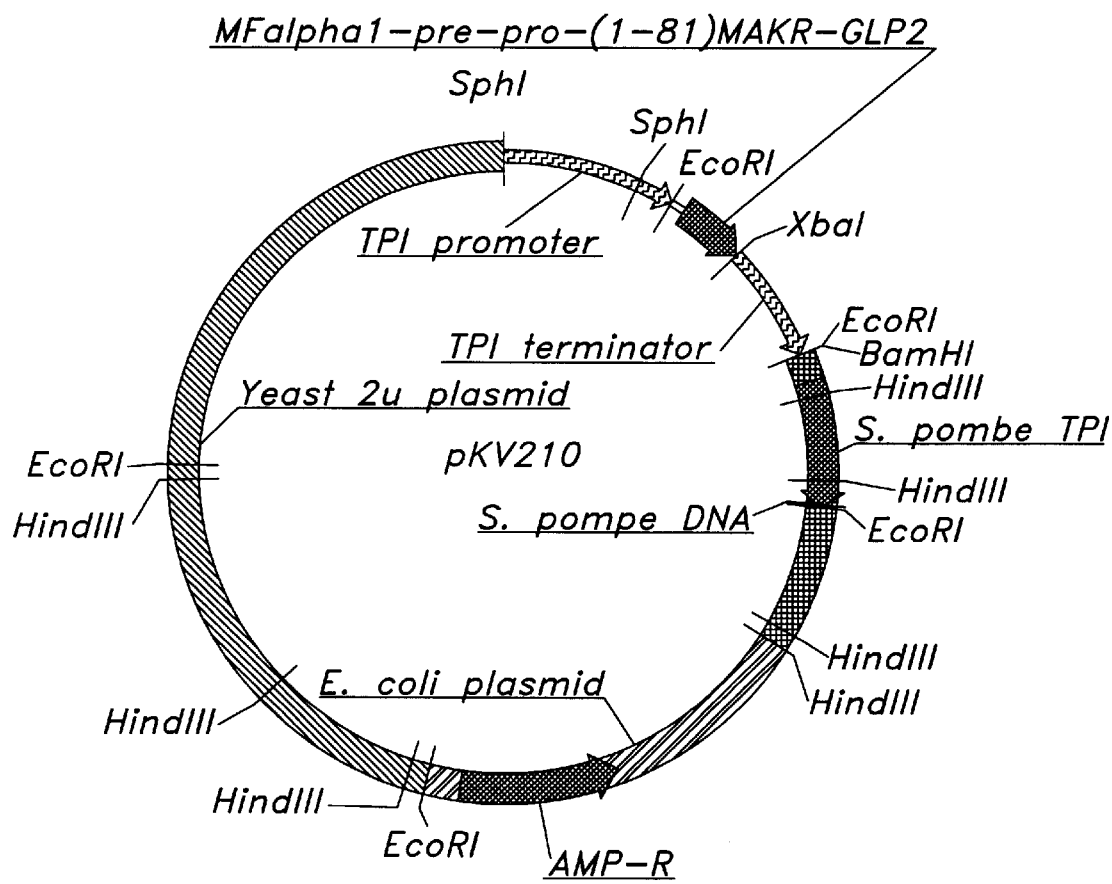
FIG. 5 is a restriction map of the human GLP-2 expression plasmid pKV210.

| Presequence (signal) | Prosequence | Heterologous protein | plasmid |
|---|---|---|---|
| MFα1(1–19) | MFα1(20–85) | Glucagon | pMT703 FIG. 3 |
| MFα1(1–19) | MFα1(20–85) | GLP-1(7–37) | pLaC253 FIG. 4 |
| MFα1(1–19) | MFα1(20–81)MAKR (SEQ ID NO:4) | GLP-2 | pKV210 FIG. 5 |
| MFα1(1–19) | MFα1(20–81)MAKR (SEQ ID NO:4) | $CRF_{1-41}$ | pKV241 |
| MFα1(1–19) | MFα1(20–81)MAKR (SEQ ID NO:4) | EEID-$CART_{55-102}$ (SEQ ID NO:2) | pSX647 |

Example 6
Expression of Glucagon

Human glucagon expression plasmid pMT703, cf. FIG. 3, was transformed into three strains, such as, YAP3 disrupted haploid strain ME1487(Δyap3), YAP3 disrupted diploid strain ME1719 (Δyap3/Δyap3) and YAP3 wild-type strain SY107 (YAP3 WT). Transformants were selected by glucose utilization as a carbon source in YPD plates (1% w/v yeast extract, 2% w/v peptone, 2% glucose, 2% agar). ME1532 and YES1746 are pMT703 transformants obtained from ME1487 (Δyap3) and ME1719 (Δyap3/Δyap3), respectively, whereas ME1530 is the pMT703 transformant obtained from SY107 (YAP3 WT). Transformants were cultivated in 5 ml YPD liquid medium at 30° C. for 3 days with shaking at 200 rpm. Culture supernatants were obtained after centrifugation at 2500 rpm for 5 min. and 1 ml supernatants were analyzed by reverse phase HPLC. Production levels, shown in Table 3, were average value of cultures from 2 independently isolated transformants (Exp. 1) or values from a mixculture of 3 transformants (Exp.2), and were normalised so that the haploid YAP3 wild-type level was taken as 100%. HPLC analyses showed that ME1532 or YES1746 produced approx. 4 to 6 times more glucagon than ME1530.

HPLC setting for glucacon detection

HPLC-Column: 4×250 mm Novo Nordisk YMC-OdDMeSi C18 5 μm

Column temp.: 50° C.

Flowrate: 1 ml/min

HPLC solvents:
  A: 10% (v/v) acetonitrile in 0.2 M $Na_2SO_4$, 0.04 M $H_3PO_4$ pH adjusted to 2.3 with ethanolamine B: 50% (v/v) acetonitrile in water Inj. vol: 150 μl Glucagon was eluated from the HPLC columns with 23.6% acetonitrile to 32.9% acetonitrile in 40 min.

TABLE 3

| TRANSFORMANT | HOST | PLASMID | GLUCAGON LEVEL | |
| --- | --- | --- | --- | --- |
| | | | Exp. 1 | Exp. 2 |
| ME1530 | SY107 | pMT703 | 100% | 100% |
| ME1532 | ME1487 | pMT703 | 596% | 469% |
| YES1746 | ME1719 | pMT703 | ND | 587% |

Example 7

Expression of GLP-1(7-37)

Human GLP-1(7-37) expression plasmid pLaC253, cf. FIG. 4, was transformed into ME1487(Δyap3), ME1719 (Δyap3/Δyap3) and SY107 (YAP3 WT). Transformants were selected and analysed as described in Example 6. ME1535 and YES1823 are the pLaC253 transformants obtained from ME1487(Δyap3) and ME1719 (Δyap3/Δyap3), respectively, whereas ME1534 is the pLaC253 transformant obtained from SY107 (YAP3 WT). Production levels, shown in Table 4, were average value of cultures from 2 independently isolated transformants (Exp. 1) or values from a mixculture of 3 transformants (Exp.2), and were normalised so that the haploid YAP3 wild-type level was taken as 100%. HPLC analyses showed that ME1535 or YES1823 produced approx. 2 to 3 times more GLP-1(7-37) than ME1530.

HPLC settings for GLP-1(7-37) detection:

As described in Example 6, except that GLP-1 was eluated from HPLC columns with

TABLE 4

| TRANSFORMANT | HOST | PLASMID | GLP-1(7–37) LEVEL | |
| --- | --- | --- | --- | --- |
| | | | Exp. 1 | Exp. 2 |
| ME1534 | SY107 | pLaC253 | 100% | 100% |
| ME1535 | ME1487 | pLaC253 | 287% | |
| YES1823 | ME1719 | pLaC253 | ND | 161% |

EXAMPLE 8

Expression of GLP-2

Human GLP-2 expression plasmid pKV210, cf. FIG. 5, was transformed into ME1487 (Δyap3), ME1719 (Δyap3/Δyap3) and SY107 (YAP3 WT). Transformants were selected and analysed as described in Example 6. ME1615 and YES1827 are the pKV210 transformants obtained from ME1487 (Δyap3) and ME1719 (Δyap3/Δyap3), respectively, whereas ME1614 is the pKV210 transformant obtained from SY107 (YAP3 WT). Production levels, shown in Table 5 were average value of cultures from 2 independently isolated transformants (Exp. 1) or values from a mixculture of 3 transformants (Exp.2), and were normalized so that the YAP3 wild-type level was taken as 100%. HPLC analyses showed that ME1615 and YES 1827 produced approx. 6 toll times more GLP-2 than ME1614.

HPLC settings for GLP-2 detection:

HPLC-Column: Vydac 214TP54 Column

Flowrate: 1 ml/min

HPLC solvents:

A: 0.1% TFA

B: 0.07% TFA in acetonitrile

GLP-2 was eluated from the HPLC columns with 0.07% TFA in 20% to 80% acetonitrile in 60 min.

TABLE 5

| TRANSFORMANT | HOST | PLASMID | GLP-2 LEVEL | |
| --- | --- | --- | --- | --- |
| | | | Exp. 1 | Exp. 2 |
| ME1614 | SY107 | pLaC210 | 100% | 100% |
| ME1615 | ME1487 | pLaC210 | 1130% | 682% |
| YES1827 | ME1719 | pLaC210 | ND | 675% |

EXAMPLE 9

Expression of $CRF_{1-41}$ (SEQ ID NO:3)

Human Corticotropin Releasing Factor ($CRF_{1-41}$) expression plasmid pKV241 (equivalent to pKV210 FIG. 5 in which MFα1-pre-pro(1-81)MAKR (SEQ ID NO:4)-GLP2 is substituted by MFα1-pre-pro(1-81)MAKR (SEQ ID NO:4)-$CRF_{1-41}$) was transformed into ME1487(Δyap3), ME1719 (Δyap3/Δyap3) and SY107 (YAP3 WT). Transformants were selected and analysed as desribed in Example 6. ME1813 and YES1810 are the pKV241 transformants obtained from ME1487(Δyap3) and ME1719 (Δyap3/Δyap3), respectively, whereas ME1812 is the pKV241 transformant obtained from SY107 (YAP3 WT). Production levels, shown in Table 6, were values from a mixculture of 3 transformants (Exp.2), and were normalised so that the haploid YAP3 wild-type level was taken as 100%. HPLC analyses were performed as in example 8 and showed that ME1813 or YES1810 produced approx. 8 to 9 times more $CRF_{1-41}$ than ME1812.

TABLE 6

| TRANSFORMANT | HOST | PLASMID | $CRF_{1-41}$ LEVEL | |
| --- | --- | --- | --- | --- |
| | | | Exp. 1 | Exp. 2 |
| ME1812 | SY107 | pKV241 | ND | 100% |
| ME1813 | ME1487 | pKV241 | ND | 834% |
| YES1810 | ME1719 | pKV241 | ND | 911% |

EXAMPLE 10

Expression of $EEID-CART_{55-102}$ (SEQ ID NO:2)

N-terminal extended (EEID) fragment of Human Cocaine and Amphetamine reg regulated transcript ($EEID-CART_{55-102}$ (SEQ ID NO:2)) expression plasmid pSX637 (equivalent to pKV210 FIG. 5, in which MFα1-pre-pro(1-81)MAKR (SEQ ID NO:4)-GLP2 is substituted by MFα1-pre-pro(1-81)MAKR (SEQ ID NO:4)-$EEID-CART_{55-102}$ (SEQ ID NO:2)), was transformed into ME1487(Δyap3), ME1719 (Δyap3/Δyap3) and SY107 (YAP3 WT). Transformants were selected and analysed as described in Example 6. ME1817 and YES1820 are the pSX637 transformants obtained from ME1487(Δyap3) and ME1719 (Δyap3/Δyap3), respectively, whereas ME1816 is the pSX637 transformant obtained from SY107 (YAP3 WT). Production levels, shown in Table 7, were values from a mixculture of 3 transformants (Exp.2), and were normalised so that the haploid YAP3 wild-type level was taken as 100%. HPLC analyses were performed as in example 8 and showed that ME1817 or YES1820 produced approx. 2 to 3 times more $EEID-CART_{55-102}$ (SEQ ID NO:2) than ME1816.

TABLE 7

| TRANSFORMANT | HOST | PLASMID | EEID-CART$_{55-102}$ LEVEL Exp. 1 | Exp. 2 |
|---|---|---|---|---|
| ME1816 | SY107 | pSX637 | ND | 100% |
| ME1817 | ME1487 | pSX637 | ND | 216% |
| YES1820 | ME1719 | pSX637 | ND | 282% |

EXAMPLE 11

Table 8 shows data for expression levels of human glucagon, GLP-1$_{(1-37)}$ and GLP-2 in ME1487 (ΔAyap3) transformed by expression plasmids with different pre-pro-sequences (leaders). Expression plasmids are as descibed in FIG. 5 except for the details given in Table 8. Expression yields are normalised so that the yield obtained in MT663 (YAP3/YAP3) transformants is set to 100%.

TABLE 8

| Presequence (signal) | Prosequence | Heterologous protein | Expression Plasmid | Yeast transformant | Yield % ME1487 |
|---|---|---|---|---|---|
| MFα1(1–19) | MFα(20–81)MAKR (SEQ ID NO:4) | Glucagon | pKV 216 | ME1652 | 267 |
| YAP3(1–21) | LA19-KR | Glucagon | pKV 225 | ME1780 | 333 |
| MFα1(1–19) | MFα(20–81)MARSKR (SEQ ID NO:9) | Glucagon | pKV 217 | ME1691 | 400 |
| MFα1(1–19) | MFα(20–81)MARKKR (SEQ ID NO:10) | Glucagon | pKV 223 | ME1692 | 185 |
| MFα1(1–19) | MFα(20–81)MAREKR (SEQ ID NO:11) | Glucagon | pKV 238 | ME1727 | 167 |
| MFα1(1–19) | MFα(20–81)MAERLE (SEQ ID NO:12) | Glucagon | pKV 237 | ME1726 | 189 |
| MFα1(1–19) | MFα(20–81)MAKELE (SEQ ID NO:13) | Glucagon | pKV 236 | ME1725 | 234 |
| MFα1(1–19) | MFα(20–81)MAKR (SEQ ID NO:4) | GLP-1$_{(1-37)}$ | pKV 230 | ME1718 | 189 |
| MFα1(1–19) | MFα(20–81)MAKR (SEQ ID NO:4) | GLP-2 A19T | pKV 219 | ME1677 | 411 |
| MFα1(1–19) | MFα(20–81)MAKR (SEQ ID NO:4) | GLP-2 A2G | pKV 220 | ME1678 | 360 |
| MFα1(1–19) | MFα(20–81)MAKR (SEQ ID NO:4) | GLP-2 F22Y | pKV 249 | ME1781 | 280 |

What is claimed is:

1. A method for the production of a heterologous short chain polypeptide in yeast, comprising (a) culturing a yeast having reduced activity of Yap3 protease, said yeast being transformed with a hybrid vector comprising a yeast promoter operably linked to a DNA sequence coding for a polypeptide having up to 55 amino acids and having from 0 to 3 disulfide bonds in the structure, and (b) isolating said polypeptide, wherein said yeast produces said short-chain polypeptide in a yield at least about 2-fold higher than a yeast transformed with said hybrid vector having a wild-type level of Yap3 protease activity.

2. A method according to claim 1, wherein the yeast lacks Yap3 protease activity.

3. A method according to claim 1, wherein the yeast is a diploid yeast.

4. A method according to claim 1 wherein the yeast additionally has reduced protease activity selected from the group of proteases coded for by BAR1, STE13, PRA, PRB, KEX1, PRC, CPS, and the YAP3 homologues MKC7, YAP3-link (coded by GenBank acc. No. X89514: pos.25352–26878), YIV9 (Swiss Prot acc. No. P40583), and aspartyl protease (IV) (coded by GenBank acc. No. U28372: pos. 326–2116) genes.

5. A method according to claim 1 wherein the yeast additionally has reduced protease activity selected from the group of proteases coded for by STE13, PRA, PRB, KEX1, and PRC genes.

6. A method according to claim 1, wherein the yeast additionally has reduced protease activity of the aparatyl protease encoded by the yeast open reading frame YGL259W or selected from the group of serine proteases coded for by the KEX2 gene and the yeast open reading frame YCR045C and YOR003W.

7. A method according to claim 1 wherein the yeast additionally has the pep4-3 mutation.

8. A method according to claim 1, wherein the hybrid vector comprises a yeast promoter operably linked to a first DNA sequence encoding a leader sequence being either a pre-sequence (signal) or a prepro-sequence linked in the proper reading frame to a second DNA sequence coding for a polypeptide having from 10–50 amino acids the and having no more than one disulfide bond in the structure, and a DNA sequence containing yeast transcription termination signals.

9. A method according to claim 1 wherein the polypeptide is selected from the group consisting of GRPP (glicentine related polypeptide), glucagon, GLP-1 (glucagon like peptide 1), and GLP-2 (glucagon like peptide 2), GLP-1(7-36), GLP-1(7-35)R36A, GLP-2 F22Y, GLP-2 A19T+34Y, GLP-2 A2G, GLP-2 A19T, and other glucagon analogues having from 1 to 3 amino acid changes, additions and/or deletions.

10. A method according to claim 1, wherein the DNA sequence encoding a polypeptide is selected from the group of DNA sequences encoding CRF and a truncated and/or N-terminally extended form of CART, preferably.

11. A method according to claim 1, wherein the yeast is selected from the group consisting of *Saccharomyces cerevisiae, Saccharomyces kluyveri, Schizosaccharomyces pombe, Kluyveromyces lactis, Hansenula polymorpha, Pichia pastoris, Pichia methanolica, Pichia kluyveri, Yarrowia lipolytica,* Candida sp., *Candida utilis, Candida cacaoi,* Geotrichum sp., and *Geotrichum fermentans.*

12. A method according to claim 1, wherein the yeast is *S. cerevisiae.*

13. A method according to claim 1, wherein the hybrid vector comprises a yeast promoter operably linked to a first DNA sequence encoding a leader sequence being either a pre-sequence (signal) or a prepro-sequence linked in the proper reading frame to a second DNA sequence coding for a polypeptide having up to 55 amino acids, and having from 0 to 3 disulfide bonds in the structure, and a DNA sequence containing yeast transcription signals.

14. A method according to claim 13, wherein the yeast promoter is selected from the group consisting of the MFα1 promoter, CYC1 promoter, galactose inducible promoters, glycolytic enzyme promoters including TPI and PGK promoters, TRP1 promoter, CUP1 promoter, PHO5 promoter, ADH1 promoter, and HSP promoters.

15. A method according to claim 13, wherein said presequence is selected from the group consisting of: the signal peptide of mouse α-amylase, S. cerevisiae MFα1, BAR1, YAP3 HSP150; and S. kluyveri MFα signal peptide; and said preprosequence is selected from the group consisting of the prepro-sequence of S. cerevisiae MFα1, YAP3, PRC, HSP150 and S. kluyveri MFα.

16. A method for the production of a heterologous open structured short chain polypeptide in yeast, comprising (a) culturing a yeast having reduced activity of Yap3 protease, said yeast being transformed with a hybrid vector comprising a yeast promoter operably linked to a DNA sequence coding for a polypeptide having from 20–30 amino acids in the polypeptide chain, and having no more than one disulfide bonds in the structure, and (b) isolating said polypeptide, wherein said yeast produces said short-chain polypeptide in a yield at least about 2-fold higher than a yeast transformed with said hybrid vector having a wild-type level of Yap3 protease activity.

17. A culture of yeast cells containing a DNA sequence encoding a heterologous polypeptide having up to 55 amino acids in the polypeptide chain, and having from 0 to 3 disulfide bonds in the structure, and a second DNA sequense encoding a leader sequence causing said polypeptide to be secreted from the yeast, wherein said culture of yeast cells has reduced Yap3p activity and wherein said yeast produces said polypeptide in a yield at least about 2-fold higher than a yeast containing said DNA sequence and having a wild-type level of Yap3 protease activity.

18. A culture of yeast cells according to claim 17 which is transformed with a hybrid vector comprising said DNA sequence and said second DNA sequence.

19. A method according to claim 18 wherein the yeast is S. cerevisiae.

* * * * *